United States Patent
Christensen

(10) Patent No.: US 9,133,144 B2
(45) Date of Patent: Sep. 15, 2015

(54) PROCESS FOR THE MANUFACTURE OF 1-[2-(2,4-DIMETHYL-PHENYLSULFANYL)-PHENYL]-PIPERAZINE

(71) Applicant: H. Lundbeck A/S, Valby (DK)

(72) Inventor: Kim Lasse Christensen, Slagelse (DK)

(73) Assignee: H. Lundbeck A/S, Copenhagen-Valby (DK)

( * ) Notice: Subject to any disclaimer, the term of this patent is extended or adjusted under 35 U.S.C. 154(b) by 0 days.

(21) Appl. No.: 14/370,322

(22) PCT Filed: Dec. 20, 2012

(86) PCT No.: PCT/EP2012/076377
§ 371 (c)(1),
(2) Date: Jul. 2, 2014

(87) PCT Pub. No.: WO2013/102573
PCT Pub. Date: Jul. 11, 2013

(65) Prior Publication Data
US 2014/0343287 A1 Nov. 20, 2014

(30) Foreign Application Priority Data
Jan. 3, 2012 (DK) .................................. 2012 00006

(51) Int. Cl.
*C07D 295/04* (2006.01)
*C07D 295/096* (2006.01)

(52) U.S. Cl.
CPC .................................. *C07D 295/096* (2013.01)

(58) Field of Classification Search
CPC .................................................... C07D 295/04
See application file for complete search history.

(56) References Cited

FOREIGN PATENT DOCUMENTS

WO       2007/144005       12/2007
WO    WO 2007144005 A1  *  12/2007

OTHER PUBLICATIONS

Bang-Andersen et al., "Discovery of 1-[(2-(2,4-Dimethylphenylsulfanyl)phenyl]piperazine (Lu AA21004): A Novel Multimodal Compound for the Treatment of Major Depressive Disorder", J. of Medicinal Chemistry, 54:3206-3221 (2011).

Bang-Andersen et al., "Discovery of 1-[2-(2,4-Dimethylphenylsulfanyl)phenyl]piperazine (Lu AA21004): A Novel Multimodal Compound for the Treatment of Major Depressive Disorder", J. of Medicinal Chemistry, 54(9) (2011), pp. S1-S45, XP007921727, retrieved from the Internet: URL:http://pubs.acs.org/doi/suppl/10.1021/jm101459g/suppl_file/jm101459g_si_001.pdf [retrieved on Apr. 2, 2013] p. S20; compound 9j.

* cited by examiner

*Primary Examiner* — Andrew D Kosar
*Assistant Examiner* — John S Kenyon
(74) *Attorney, Agent, or Firm* — Fish & Richardson P.C.

(57) ABSTRACT

A process for the manufacture of 1-[2-(2,4-dimethyl-phenyl-sulfanyl)-phenyl]-piperazine and pharmaceutically acceptable salts is disclosed that involves reacting compounds of formula II, III, IV under Pd catalysis and in presence of phosphine ligands to give Compound I.

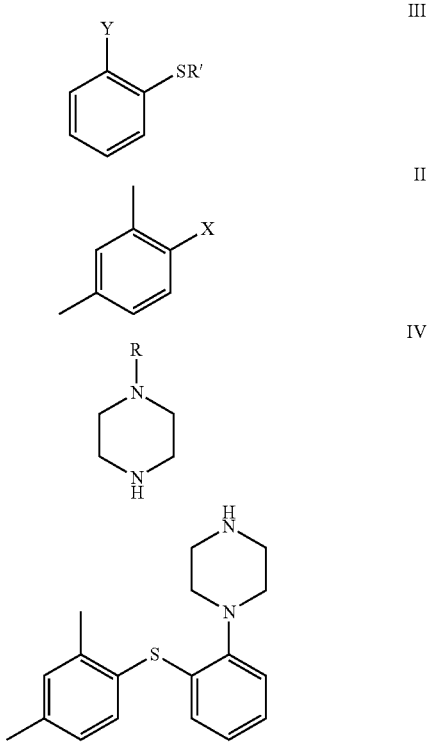

18 Claims, No Drawings

PROCESS FOR THE MANUFACTURE OF 1-[2-(2,4-DIMETHYL-PHENYLSULFANYL)-PHENYL]-PIPERAZINE

FIELD OF THE INVENTION

The present invention relates to a process for the manufacture of the compound 1-[2-(2,4-dimethyl-phenylsulfanyl)-phenyl]-piperazine and pharmaceutically acceptable salts thereof.

BACKGROUND OF THE IN INVENTION

The international patent applications WO 03/029232 and WO 2007/144005 disclose the compound 1-[2-(2,4-dimethyl-phenylsulfanyl)-phenyl]-piperazine including various manufacturing routes. In the remainder of this document, 1-[2-(2,4-dimethyl-phenylsulfanyl)-phenyl]-piperazine and pharmaceutically acceptable salts thereof are respectively referred to as Compound I and Compound I XX when reference to the XX salt is desired.

Compound I is an antagonist on the 5-HT$_3$, 5-HT$_7$ and 5-HT$_{1D}$ receptors, an agonist on the 5-HT$_{1A}$ receptor and a partial agonist on the 5-HT$_{1B}$ receptor and an inhibitor of the serotonin transporter. Additionally, Compound I has demonstrated to enhance the levels of the neurotransmitters serotonin, noradrenalin, dopamine, acetylcholine and histamine in specific areas of the brain. All of these activities are considered to be of clinical relevance and potentially involved in the mechanism of action of the compound [*J. Med. Chem.*, 54, 3206-3221, 2011; *Eur. Neuropshycopharmacol.*, 18(suppl 4), S321, 2008; *Eur. Neuropshycopharmacol.*, 21(suppl 4), S407-408, 2011; *Int. J. Psychiatry Clin Pract.* 5, 47, 2012].

Compound I has in clinical trials shown to be a safe and efficacious treatment for depression. A paper reporting the results from a proof-of-concept study to evaluate the efficacy and tolerability of the compound in patients with major depressive disorder (MDD) authored by Alvares et at was made available on-line by *Int. J. Neuropsychopharm.* 18 Jul. 2011. The results from this six weeks, randomised, placebo-controlled study with approximately 100 patients in each arm show that Compound I separates significantly from placebo in the treatment of depressive and anxious symptoms in patients with MDD. It is also reported that no clinically relevant changes were seen in the clinical laboratory results, vital signs, weight, or ECG parameters. Results from a long-term study also show that Compound I is effective in preventing relapse in patients suffering from MDD [*Eur. Neuropsychopharmacol.* 21(suppl 3), S396-397, 2011].

WO 2007/144005 discloses a manufacturing process in which the compounds

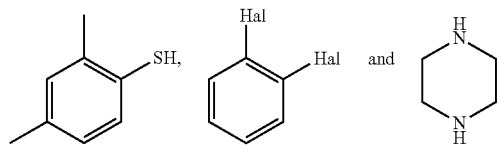

are mixed in the presence of a base and a palladium catalyst consisting of a palladium source and a phosphine ligand. The palladium catalysts catalyses the formation of the C—N bond as disclosed in U.S. Pat. No. 5,573,460. In the above process, the piperazine may optionally be protected at one of the nitrogens. This process gives the desired compound in a high yield and with a relatively high purity. Nevertheless, impurities are formed which subsequently have to be removed. It is particularly difficult to remove impurities which like compound I contain secondary amine, i.e. a piperazine moiety. Such compounds tend to have similar solubility properties, e.g. including pH-dependent solubility properties, and are thus difficult to separate from Compound I using methods that take advantage of differences in solubility, e.g. crystallisation. WO 2010/094285 discloses a purification process which effectively removes such impurities, e.g. 1-[2-(2,4-dimethyl-phenylsulfanyl)-phenyl]-4-(2-piperazin-1-yl-phenyl)-piperazine which is formed when both nitrogens in the piperazine group form a C—N bond. The purification process comprises precipitating an isopropanol solvate of Compound I, HBr.

The present invention provides a new manufacturing route which eliminates or reduces the above mentioned difficult-to-remove impurities.

SUMMARY OF THE INVENTION

The inventor has found that a reaction between 1-halogen-2,4-dimethyl-phenyl, 2-halogen-thiophenol and an optionally protected piperazine in the presence of a base and a palladium catalyst provides for a reaction with high yield and purity, and wherein impurities are reduced or eliminated. Accordingly, in one embodiment the invention relates to a process for the manufacture of

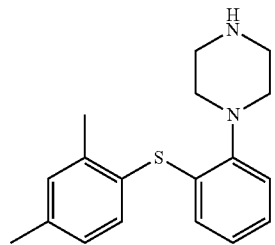 [SMILES: Cc1ccc(Sc2ccccc2N2CCNCC2)c(C)c1]

(Compound I) or pharmaceutically acceptable salts thereof, said process comprising reacting a compound of formula II

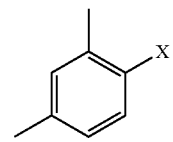

II wherein X represents Br or I, with a compound of formula III

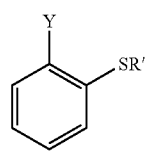

III wherein Y represents Cl or Br and R' represents hydrogen or a metal ion, and a compound of formula IV

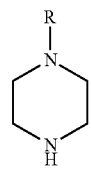

IV wherein R represents hydrogen or a protective group, in the presence of a solvent, a base and a palladium catalyst consisting of a palladium source and a phosphine ligand at a temperature between 50° C. and 130° C.

DETAILED DESCRIPTION OF THE INVENTION

In one embodiment, compound of formula II and compound of formula III may be reacted in a first step to prepare the intermediate

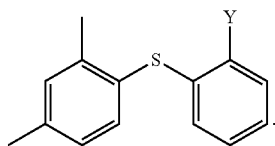

This intermediate may then be isolated before further reaction with a compound of formula IV to obtain Compound I. Alternatively, this further reaction may take place without isolating the intermediate. One-pot synthesis, i.e. synthesis routes wherein all the reactant are charged to the reactor at the start of the reaction without isolation or purification of intermediates are generally preferred routes due to their inherent simplicity. On the other hand, the number of possible, unwanted side reactions is also increased in one-pot synthesis with the corresponding increase in side products and loss of yield. For the present process it is noted that piperazine contains two identical secondary amines which could both potentially take part in the formation of a C—N bond. Nevertheless, it has been found that the present manufacturing route is highly effective in avoiding such side reactions. In particular, it has been found that the present manufacturing process effectively avoids or reduces the formation of impurities formed by C—N bond formation involving the secondary amine in Compound I. Examples of such impurities include 1-(2,4-dimethyl-phenyl)-4-[2-(2,4-dimethyl-phenylsulfanyl)-phenyl]-piperazine.

WO 2010/094285 discloses a purification process which can be used to remove impurities generated when the second amine in the piperazine moiety also participates in the formation of a C—N bond. The purification process disclosed in WO 2010/094285 is applied to a process for the manufacture of Compound I in which 2,4-dimethyl-thiophenol, 1,2-dihalobenzene and optionally substituted piperazine are reacted in the presence of a palladium catalysts. This process was first disclosed in WO 2005/144005 WO 2007/144005. The data provided in WO2010/094285 seems to indicate that impurities formed when the second amine also participates in the formation of a C—N bond in this reaction, e.g. 1-[2-(2,4-dimethyl-phenyl-sulfanyl)-phenyl]-4-(2-piperazin-1-yl-phenyl)-piperazine is generated in an amount of 0.5% to 4.8%. This is consistent with the data shown in Example 4 in the present application, wherein 1% of this impurity is generated. As discussed below, the palladium catalyst also catalyses formation of C—S bonds. It is furthermore noted that in the manufacturing process of the present invention impurities generated by the reaction of two (or more) thiol compounds (compound of formula III) are not generated in any meaningful amount.

As shown in the examples, the present invention provides an alternative manufacturing process for Compound I in which little or no impurities are generated via C—N bond formation at the second piperazine nitrogen. At the same time, the total impurity level is also reduced compared to the process disclosed in WO 2007/144005 and the overall yield is maintained at a high level. Furthermore, the manufacturing process of the present invention provides a simpler overall process in that purification steps to remove impurities generated via formation of C—N bond at the second piperazine nitrogen, e.g. as disclosed in WO 2010/094285, can be avoided. The data shown in examples 1-4 show that impurities generated when the second amine participates in C—N bond formation, e.g. Impurity E, are for all practical purposes not formed. This compares favourably with the level of such impurities around 1% with the process of WO 2007/144005 as demonstrated in example 4 and the even larger numbers reported in WO 2010/094285. It is also noted that the overall level of impurities is significantly lower, i.e. about 50% lower, with the manufacturing process of the present invention which again means that the purity of Compound I as obtained in the manufacturing process of the present invention is much higher.

The compound of formula II is 1-halogen-2,4-dimethyl-phenyl wherein said halogen is selected from Br and I. In one embodiment, the compound of formula II is 1-iodo-2,4-dimethyl-phenyl.

The compound of formula III is 2-halogen-thiophenol, wherein said halogen is selected from Cl and Br. In one embodiment, the compound of formula III is 2-bromo-thiophenol.

The compound of formula III is a thiol or the corresponding thiolate. Due to the basic reaction conditions, the reacting species is thiolate. From a occupational health perspective is may be beneficial to use a thiolate, such as the $Li^+$, $Na^+$, $K^+$ or $Ca^{++}$ thiolate to avoid the odour problems associated with thiols. Nonetheless, in one embodiment, R' is hydrogen.

The compounds of formula II and III are typically added in equi-molar amounts, and these compounds are also typically added in a limiting amount.

The compound of formula IV is a piperazine compound. Piperazine has two nitrogens, only one of which is to participate in the C—N bond formation. In one embodiment, formation of bonds to the second nitrogen is avoided by using a mono-protected piperazine, i.e. an embodiment wherein R is a protective group. Many protective groups are known in the art, and useful examples include —C(=O)O—W, —C(=O)—W, boc, Bn and Cbz, and in particular boc. W represents alkyl or aryl; Bn abbreviates benzyl; boc abbreviates t-butyloxycarbonyl; and cbz abbreviates benzyloxycarbonyl. If a protected piperazine is used in the reactions, the protective group has to be removed in a subsequent step, typically by the addition of aqueous acid. The present process has been found to give rise to only low levels of impurities generated via the formation of a C—N bond at the second piperazine amine. This allows for the use of un-protected piperazine (i.e. R is hydrogen). The use of unprotected piperazine allows for an inherently simpler process in that the de-protection step can be avoided.

The compound of formula IV is typically added in 1-100 equivalents, such as 1-10 equivalents, typically 1-3 equivalents. Alternatively, piperazine may be used as the solvent, i.e. an embodiment wherein piperazine is both reactant and solvent.

The solvent used in the process of the present invention may be selected from aprotic organic solvents or mixtures of such solvents with a boiling temperature within the reaction temperature range, i.e. 50-130° C. Typically, the solvent is selected from amongst toluene, xylene, triethyl amine, tributyl amine, dioxan, N-methylpyrrolidone, pyridine or from any mixture thereof. Particular mention is made of toluene as solvent.

Central to the present process is the use of a palladium catalyst without which Compound I is not formed. As discussed above, the palladium catalyst catalyses the formation of the C—N bond but also the formation of the C—S bond [*Bull. Chem. Soc. Jpn.*, 53, 1385-1389, 1980]. The palladium catalyst consists of a palladium source and a phosphine ligand. Useful palladium sources include palladium in different oxidations states, such as e.g. 0 and II. Examples of palladium sources which may be used in the process of the present invention are $Pd_2(dba)_3$, $Pd(dba)_2$ and $Pd(OAc)_2$. dba abbreviates dibenzylideneacetone. Particular mention is made of $Pd(dba)_2$ and $Pd(OAc)_2$. The palladium source is typically applied in an amount of 0.1 and 6 mole-%, such as 0.5 and 2 mole-%, typically around 1 mole-%. Throughout this application, mole-% and equivalent are calculated with respect to the limiting reactant.

Numerous phosphine ligands are known, both monodentate and bidentate. Useful phosphine ligands include racemic 2,2'-bis-diphenylphosphanyl-[1,1']binaphtalenyl (rac-BINAP), (S)-BINAP, (R)-BINAP, 1,1'-bis(diphenylphosphino) ferrocene (DPPF), bis-(2-diphenylphosphinophenyl)ether (DPEphos), tri-t-butyl phosphine (Fu's salt), biphenyl-2-yl-di-t-butyl-phosphine, biphenyl-2-yl-dicyclohexyl-phosphine, (2'-dicyclohexylphosphanyl-biphenyl-2-yl)-dimethyl-amine, [2'-(di-t-butyl-phosphanyl)-biphenyl-2-yl]-dimethyl-amine, and dicyclohexyl-(2',4',6'-tri-propyl-biphenyl-2-yl)-phosphane. Moreover, carbene ligands, such as e.g. 1,3-bis-(2,6-di-isopropyl-phenyl)-3H-imidazol-1-ium; chloride may be used in stead of phosphine ligands. In one embodiment, the phosphine ligand is rac-BINAP, DPPF or DPEphos, and in particular rac-BINAP. The phosphine ligand is usually applied in an amount between 0.2 and 12 mole-%, such as 0.5 and 4 mole-%, typically around 2 mole-%.

Base is added to the reaction mixture to increase pH. In particular bases selected from NaOt-Bu, KOt-Bu, $Na_2CO_3$, $K_2CO_3$ and $Cs_2CO_3$ are useful. Organic bases, such as 1,8-diazabicyclo[5.4.0]undec-7-ene (DBU) and 1,4-diazabicyclo[2.2.2]octane (DABCO) may be applied as well. Particular mention is made of NaO(t-Bu) and KO(t-Bu). Typically, the base is added is an amount around 2-10 equivalents, such as 2-5 equivalents, such as 2.5-3.5 equivalents.

In some situations it may be desirable to obtain an acid addition salt of 1-[2-(2,4-dimethyl-phenylsulfanyl)-phenyl]-piperazine rather than the free base. Acid addition salts may be achieved in a further process step in which the free base obtained is reacted with a relevant acid, such as e.g. lactic acid, hydrochloric acid or hydrobromic acid. The acid may be added directly to the reaction mixture or, alternatively, the free base may be purified to any suitable degree initially before such step. If the free base has been isolated as a solid compound, it may be necessary to use a solvent in order to bring the free base into solution prior to a reaction with the acid. In one embodiment, aqueous hydrobromic acid is added directly to the reaction mixture without any initial purification of the free base. Alternatively, HBr may be added in an alcoholic solution.

In processes wherein a protected piperazine is used, the protective group has to be removed e.g. by the addition of an aqueous acid as explained above. In one embodiment, said aqueous acid may be selected to achieve two transformations, i.e. the de-protection of the protected piperazine and the formation of an acid addition salt. In particular, aqueous hydrobromic acid may be used to de-protect protected piperazine and to obtain the hydrobromic acid addition salt in one process step.

In one embodiment, the process of the present invention is run at 75°-120°, or at 80°-120°.

It goes for all the reactions and reaction mixtures mentioned here that it may be an advantage to purge them with an inert gas or run them under a blanket of inert gas. Nitrogen is a cheap and readily available example of an inert gas.

In one embodiment, Compound I is prepared in a process which comprises reacting

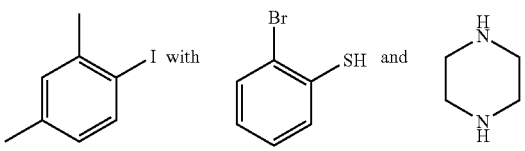

in the presence of a solvent, a base and a palladium catalyst consisting of a palladium source and a phosphine ligand at a temperature between 50° C. and 130° C. In a further embodiment the compound obtained is reacted with an acid to obtain a desired pharmaceutically acceptable salt of 1-[2-(2,4-dimethyl-phenylsulfanyl)-phenyl]-piperazine.

In one embodiment, the invention provides a process for the manufacture of Compound I, which process comprises the steps of a) Dissolving or dispersing 0.1 mole-%-3 mole-% bis(dibenzylideneacetone)-palladium(0) and 0.5 mole-%-4 mole-% racemic 2,2'-bis-diphenylphosphanyl-[1,1']binaphtalenyl and 2-6 equivalents base in toluene to obtain Mixture A;

b) adding 1 equivalent 1-iodo-2,4-dimethylbenzene, 0.8-1.2 equivalent 2-bromo thiophenol and 1-10 equivalents piperazine to Mixture A and to obtain Mixture B; and c) heating Mixture B to 80° C.-120° C. or 75°-120° to obtain

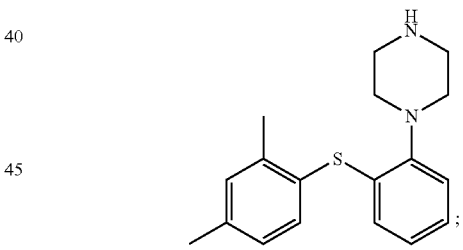

and d) optionally adding an appropriate acid to the product obtained in step c) to obtain the corresponding salt. Particular mention is made of addition of aqueous HBr.

In one embodiment, the invention relates to Compound I and in particular Compound I HBr obtained in a process comprising or consisting of steps a) through d) above.

In one embodiment, the invention provides a process for the manufacture of Compound I, which process comprises the steps of a) Dissolving or dispersing 0.1 mole-%-3 mole-% bis(dibenzylideneacetone)-palladium(0) and 0.5 mole-%-4 mole-% racemic 2,2'-bis-diphenylphosphanyl-[1,1']binaphtalenyl, 1-10 equivalents piperazine and 2-6 equivalents base in toluene to obtain Mixture A;

b) adding 1 equivalent 1-iodo-2,4-dimethylbenzene and 0.8-1.2 equivalent 2-bromo thiophenol to Mixture A to obtain Mixture B; and c) heating Mixture B to 80° C.-120° C. or 75°-120° to obtain

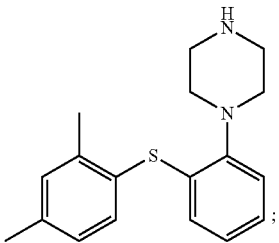 [SMILES: Cc1ccc(Sc2ccccc2N2CCNCC2)c(C)c1]

and d) optionally adding an appropriate acid to the product obtained in step c) to obtain the corresponding salt. Particular mention is made of addition of aqueous HBr.

In one embodiment, the invention relates to Compound I and in particular Compound I HBr obtained in a process comprising or consisting of steps a) through d) above.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

The use of the terms "a" and "an" and "the" and similar referents in the context of describing the invention are to be construed to cover both the singular and the plural, unless otherwise indicated herein or clearly contradicted by context. For example, the phrase "the compound" is to be understood as referring to various compounds of the invention or particular described aspect, unless otherwise indicated.

The description herein of any aspect or aspect of the invention using terms such as "comprising", "having," "including," or "containing" with reference to an element or elements is intended to provide support for a similar aspect or aspect of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

EXAMPLES

Example 1

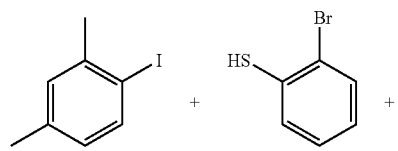

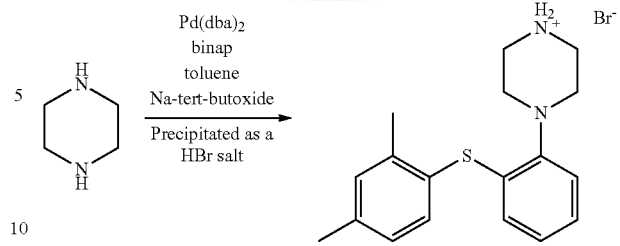

Bis(dibenzylideneacetone)palladium(0) (0.610 g, 1.06 mmol), racemic 2,2'-bis(diphenylphosphino)-1,1'-binaphthyl (1.34 g, 2.15 mmol), sodium tert-butoxide (31.0 g, 323 mmol) and toluene (150 mL, de-gassed) were mixed. The reaction mixture was stirred for 2 hours at room temperature (23° C.) under an atmosphere of nitrogen.

To this mixture were added piperazine (23.0 g, 267 mmol), 1-iodo-2,4-dimethylbenzene (25.0 g, 108 mmol) and 2-bromo thiophenol (20.5 g, 108 mmol), The reaction mixture was then heated at 100° C. for 5 hours, after which it was cooled to room temperature. To reaction mixture was added water (80 mL) (IPC (In Process Control) sampled here) and then Celite 545 (8.0 g). The reaction was stirred for 20 minutes before filtration. The phases were separated and the toluene phase was washed 2 times with water (2×80 mL).

The toluene phase was heated at 60° C. To the warm toluene phase was added hydrobromic acid (8.9 M, 13.0 mL, 116 mmol), seeding crystals ((HBr salt) of the title compound, 10 mg) were added and the solution was allowed to cool to room temperature.

1-[2-(2,4-Dimethyl-phenylsulfanyl)-phenyl]-piperazine, HBr was isolated by filtration and the filter cake was washed 2 times with toluene (2×30 mL).

Yield 80.1% of 1-[2-(2,4-dimethyl-phenylsulfanyl)-phenyl]-piperazine, HBr (33.5 g, 88.3 mmol).

Purity 97.9% (HPLC, UV detection at 254 nm)

$^1$H NMR (DMSO-$d_6$; 500 MHz): 8.83 (bs, 2H), 7.34 (d, 1H), 7.26 (s, 1H), 7.15 (m, 3H), 6.98 (dd, 1H), 6.43 (d, 1H), 3.26 (bm, 4H), 3.21 (bm, 4H), 2.33 (s, 3H), 2.25 (s, 3H).

Example 2

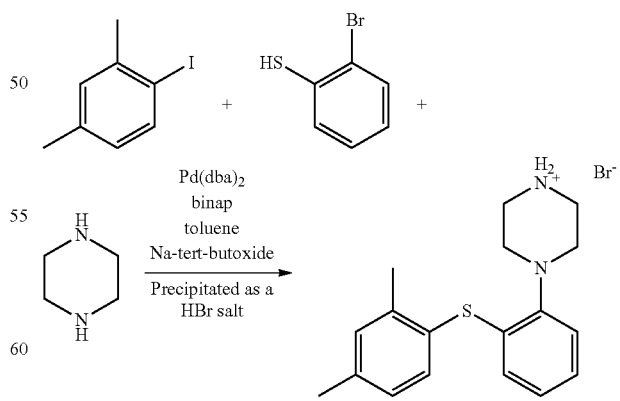

Bis(dibenzylideneacetone)palladium(0) (665 mg, 1.15 mmol), racemic 2,2'-bis(diphenylphosphino)-1,1'-binaphthyl (1.44 g, 2.30 mmol), sodium tert-butoxide (22.2 g, 231 mmol), piperazine (16.6 g, 193 mmol), and toluene (110 mL, de-gassed) were mixed. The reaction mixture was stirred for 1 hour at room temperature (23° C.) under an atmosphere of nitrogen.

To this mixture were added 1-iodo-2,4-dimethylbenzene (15.1 g, 65.0 mmol) and 2-bromo thiophenol (11.8 g, 62.4 mmol), The reaction mixture was then heated at 100° C. for 4 hours, after which it was cooled to room temperature. To reaction mixture was added water (60 mL) (IPC sampled here) and then Celite 545 (9.5 g). The reaction was stirred for 20 minutes before filtration. The phases were separated and the toluene phase was washed 2 times with water (2×60 mL).

The toluene phase was heated at 60° C. To the warm toluene phase was added hydrobromic acid (8.9 M, 9.3 mL, 82.8 mmol), seeding crystals (HBr salt of the title compound, 10 mg) were added and the solution was allowed to cool to room temperature.

1-[2-(2,4-Dimethyl-phenylsulfanyl)-phenyl]-piperazine, HBr was isolated by filtration and the filter cake was washed 3 times with toluene (3×25 mL).

Yield 77.1% of 1-[2-(2,4-dimethyl-phenylsulfanyl)-phenyl]-piperazine, HBr (18.6 g, 49.0 mmol).

Purity 98.2% (HPLC, UV detection at 254 nm)

$^1$H NMR (DMSO-$d_6$): 8.83 (bs, 2H), 7.34 (d, 1H), 7.26 (s, 1H), 7.14 (m, 3H), 6.97 (dd, 1H), 6.42 (d, 1H), 3.26 (bm, 4H), 3.21 (bm, 4H), 2.33 (s, 3H), 2.25 (s, 3H).

Example 3

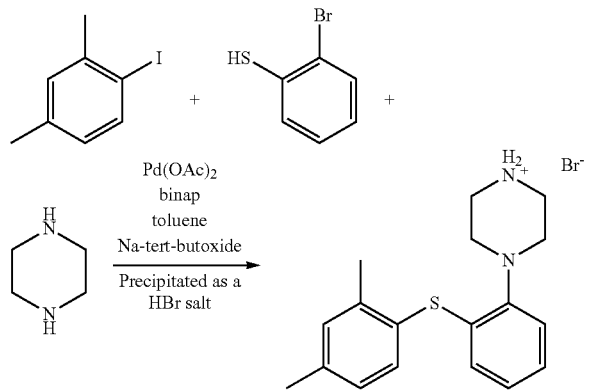

Palladium(II) acetate (580 mg, 2.58 mmol), racemic 2,2'-bis(diphenylphosphino)-1,1'-binaphthyl (3.20 g, 5.16 mmol), sodium tert-butoxide (49.5 g, 516 mmol), piperazine (37.0 g, 430 mmol), and toluene (250 mL, de-gassed) were mixed. The reaction mixture was stirred for 2 hours at room temperature (23° C.) under an atmosphere of nitrogen.

To this mixture were added 1-iodo-2,4-dimethylbenzene (40.0 g, 172 mmol) and 2-bromo thiophenol (32.6 g, 172 mmol), The reaction mixture was then heated at 100° C. for 1 hour, after which it was cooled to room temperature. To reaction mixture was added water (80 mL) (IPC sampled here) and then Celite 545 (12 g). The reaction was stirred for 20 minutes before filtration. The phases were separated and the toluene phase was washed 2 times with water (2×80 mL).

The toluene phase was heated at 60° C. To the warm toluene phase was added hydrobromic acid (8.9 M, 20.8 mL, 185 mmol), seeding crystals (HBr salt of the title compound, 10 mg) were added and the solution was allowed to cool to room temperature.

1-[4-(2,4-Dimethyl-phenylsulfanyl)-phenyl]-piperazine, HBr was isolated by filtration and the filter cake was washed 3 times with toluene (3×40 mL).

Yield 84.3% of 1-[2-(2,4-dimethyl-phenylsulfanyl)-phenyl]-piperazine, HBr containing 0.60 eq of tert-butanol (62.1 g, 147 mmol).

Purity 98.6% (HPLC, UV detection at 254 nm).

$^1$H NMR (DMSO-$d_6$): 8.82 (bs, 2H), 7.34 (d, 1H), 7.26 (s, 1H), 7.15 (mp, 3H), 6.98 (dd, 1H), 6.43 (d, 1H), 3.27 (bm, 4H), 3.21 (bm, 4H), 2.34 (s, 3H), 2.25 (s, 3H), 1.12 (s, 5.4H).

Example 4

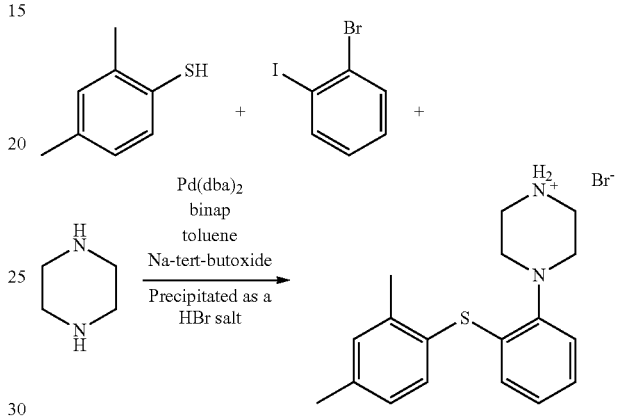

Bis(dibenzylideneacetone)palladium(0) (307 mg, 0.530 mmol), racemic 2,2'-bis(diphenylphosphino)-1,1'-binaphthyl (0.66 g, 1.06 mmol), sodium tert-butoxide (44.7 g, 466 mmol), piperazine (40.3 g, 469 mmol) and toluene (200 mL, de-gassed) were mixed. The reaction mixture was stirred for 35 minutes at room temperature (23° C.) under an atmosphere of nitrogen.

To this mixture were added 1-bromo-2-iodo-benzene (39.2 g, 135 mmol) and 2,4-dimethyl-benzenethiol (18.3 g, 133 mmol), The reaction mixture was then heated at reflux for 6 hours, after which it was cooled to room temperature. To the reaction mixture was added water (60 mL) (IPC sampled here) and then Celite 545 (9.0 g). The reaction was stirred for 20 minutes before filtration. The phases were separated and the toluene phase was washed 2 times with water (2×60 mL).

The toluene phase was heated at 60° C. To the warm toluene phase was added hydrobromic acid (8.9 M, 16.8 mL, 150 mmol), seeding crystals (HBr salt of the title compound, 10 mg) were added and the solution was allowed to cool to room temperature.

1-[2-(2,4-Dimethyl-phenylsulfanyl)-phenyl]-piperazine, HBr was isolated by filtration and the filter cake was washed 3 times with toluene (3×25 mL).

Yield 81.5% of 1-[2-(2,4-dimethyl-phenylsulfanyl)-phenyl]-piperazine, HBr containing 0.70 eq of tert-butanol (51.2 g, 118 mmol).

Purity 96.0% (HPLC, UV detection at 254 nm).

$^1$H NMR (DMSO-$d_6$): 8.78 (bs, 2H), 7.34 (d, 1H), 7.26 (s, 1H), 7.15 (m, 3H), 6.98 (dd, 1H), 6.43 (d, 1H), 3.27 (bm, 4H), 3.20 (bm, 4H), 2.34 (s, 3H), 2.26 (s, 3H), 1.12 (s, 6.3H).

The table below shows analytical data on impurities (Area-% by hplc) for IPC and final product for examples 1-4.

HPLC-Method

Column type: Acquity UPLC BEH C18 1.7 μm; 2.1×150 mm

Column temperature: 60° C.

Detection at 254 nm
Flow: 0.6 ml/min.
Solvents:
  A: Water containing 0.05% TFA (trifluoroacetic acid)
  B: Acetonitrile containing 5% Water and 0.035% TFA

| Gradient: | | |
|---|---|---|
| Time, min. | % B | Curve |
| 0.00 | 10.0 | 6 |
| 1.80 | 99.9 | 6 |
| 1.81 | 10.0 | 6 |
| 2.00 | 10.0 | 6 |

Impurity A is 1,2-bis(1'-piperazinyl)benzene.
Impurity B is 1-phenyl-piperazine.
Impurity C is 1-(2-bromo-phenyl)piperazine.
Impurity D is 1-(2,4-dimethyl-phenyl)-piperazine.
Impurity E is 1-[2-(2,4-dimethyl-phenylsulfanyl)-phenyl]-4-(2-piperazin-1-yl-phenyl)-piperazine.
Impurity F is 1-(2,4-dimethyl-phenyl)-4-[2-(2,4-dimethyl-phenylsulfanyl)-phenyl]piperazine.
Impurity G is 2,4-dimethyl-1-phenylsulfanylbenzene.

| | Example 1 | | Example 2 | | Example 3 | | Example 4 | |
|---|---|---|---|---|---|---|---|---|
| Impurity | IPC | Final product | IPC | Final product | IPC | Final product | IPC | Final product |
| A | <0.05 | <0.05 | <0.05 | <0.05 | <0.05 | <0.05 | 4.1 | 2.4 |
| B | <0.05 | <0.05 | <0.05 | <0.05 | <0.05 | <0.05 | 0.4 | 0.3 |
| C | <0.05 | <0.05 | <0.05 | <0.05 | <0.05 | <0.05 | 0.1 | <0.05 |
| D | 0.2 | <0.05 | 1.0 | <0.05 | 1.4 | <0.05 | <0.05 | <0.05 |
| E | <0.05 | <0.05 | <0.05 | <0.05 | <0.05 | <0.05 | 1.0 | 1.1 |
| F | <0.05 | <0.05 | <0.05 | <0.05 | <<0.05 | <0.05 | <0.05 | <0.05 |
| G | 1.8 | <0.05 | 1.2 | <0.05 | 1.6 | <0.05 | 2.8 | <0.05 |
| Comp I | 91.4 | 97.9 | 91.3 | 98.6 | 90.8 | 98.2 | 87.6 | 96.0 |
| Total impurities | 8.6 | 2.1 | 8.7 | 1.4 | 9.2 | 1.8 | 12.4 | 4.0 |

The invention claimed is:

1. A process for the manufacture of

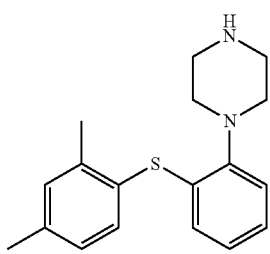 [SMILES: Cc1ccc(Sc2ccccc2N2CCNCC2)c(C)c1]

(Compound I) or pharmaceutically acceptable salts thereof, said method comprising reacting a compound of formula II

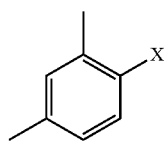

II wherein X represents Br or I, with a compound of formula III

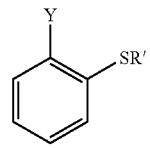

III wherein Y represents Cl or Br and R' represents hydrogen or a metal ion, and a compound of formula IV

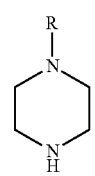

IV wherein R represents hydrogen or a protective group, in the presence of a solvent, a base and a palladium catalyst consisting of a palladium source and a phosphine ligand at a temperature between 50° C. and 130° C., provided that when R represents a protective group, said protective group is removed in a subsequent step.

2. The process according to claim 1, wherein X represents I.

3. The process according to claim 1, wherein Y represents Br and R' represents H.

4. The process according to claim 1, wherein R represents H.

5. The process according to claim 1, wherein R represents a protective group selected from the group consisting of —C(=O)O—W, —C(=O)—W, boc, Bn and Cbz, wherein W represents alkyl or aryl.

6. The process according to claim 1, wherein said solvent is an aprotic solvent.

7. The process according to claim 6, wherein said solvent is toluene.

8. The process according to claim 1, wherein said palladium source is selected from the group consisting of Pd(dba)$_2$, Pd(OAc)$_2$ and Pd$_2$dba$_3$.

9. The process according to claim 8, wherein said palladium source is Pd(dba)$_2$ or Pd(OAc)$_2$.

10. The process according to claim 1, wherein said phosphine ligand is selected from the group consisting of
  racemic 2,2'-bis-diphenylphosphanyl-[1,1']binaphtalenyl (rac-BINAP),
  1,1'-bis(diphenylphosphino)ferrocene (DPPF), bis-(2-diphenylphosphinophenyl)ether (DPEphos),
tri-t-butyl phosphine (Fu's salt),
biphenyl-2-yl-di-t-butyl-phosphine,
biphenyl-2-yl-dicyclohexyl-phosphine,
(2'-dicyclohexylphosphanyl-biphenyl-2-yl)-dimethyl-amine
[2'-(di-t-butyl-phosphanyl)-biphenyl-2-yl]-dimethyl-amine, and
dicyclohexyl-(2',4',6'-tri-propyl-biphenyl-2-yl)-phosphane.

11. The process according to claim 10, wherein said phosphine ligand is 2,2'-bis-diphenylphosphanyl-[1,1']binaphtalenyl (rac-BINAP).

12. The process according to claim 1, wherein said base is selected from the group consisting of NaO(t-Bu), KO(t-Bu), K₂CO₃, Na₂CO₃, Cs₂CO₃, DBU and DABCO.

13. The process according to claim 12, wherein said base is NaO(t-Bu).

14. The process according to claim 1, further comprising reacting the product obtained with an appropriate acid to remove the protective group (when R is a protective group) and/or to obtain the desired pharmaceutically acceptable salt.

15. The process according to claim 1, which comprises reacting

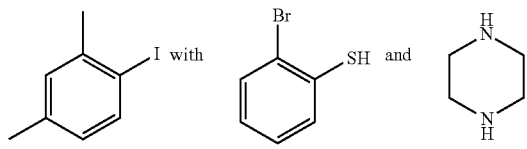

in the presence of a solvent, a base and a palladium catalyst consisting of a palladium source and a phosphine ligand at a temperature between 50° C. and 130° C.

16. The process according to claim 15, further comprising reacting the compound obtained with an acid to obtain a desired pharmaceutically acceptable salt of said compound.

17. The process according to claim 1, comprising the steps of
a) dissolving or dispersing 0.1 mole-%-3 mole-% bis(dibenzylideneacetone)-palladium(0) and 0.5 mole-%-4 mole-% racemic 2,2'-bis-diphenylphosphanyl-[1,1']binaphtalenyl and 2-6 equivalents base in toluene to obtain Mixture A;
b) adding 1 equivalent 1-iodo-2,4-dimethylbenzene, 0.8-1.2 equivalent 2-bromo thiophenol and 1-10 equivalents piperazine to Mixture A to obtain Mixture B; and
c) heating Mixture B to 80° C.-120° C. to obtain

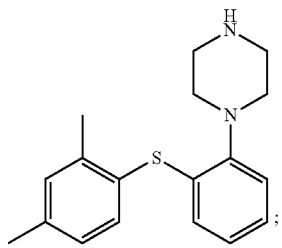 [SMILES: Cc1ccc(Sc2ccccc2N2CCNCC2)c(C)c1]

and
d) optionally adding an appropriate acid to the product obtained in step c) to obtain the corresponding salt.

18. A The process according to claim 1, comprising the steps of
a) dissolving or dispersing 0.1 mole-%-3 mole-% bis(dibenzylideneacetone)-palladium(0), 0.5 mole-%-4 mole-% racemic 2,2'-bis-diphenylphosphanyl-[1,1']binaphtalenyl, 1-10 equivalents piperazine and 2-6 equivalents base in toluene to obtain Mixture A;
b) adding 1 equivalent 1-iodo-2,4-dimethylbenzene and 0.8-1.2 equivalent 2-bromo thiophenol to Mixture A to obtain Mixture B; and
c) heating Mixture B to 80° C.-120° C. to obtain

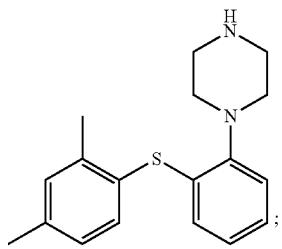 [SMILES: Cc1ccc(Sc2ccccc2N2CCNCC2)c(C)c1]

and
d) optionally adding an appropriate acid to the product obtained in step c) to obtain the corresponding salt.

* * * * *